United States Patent [19]

Donahoo

[11] Patent Number: 4,564,008
[45] Date of Patent: Jan. 14, 1986

[54] ARM SUPPORT APPARATUS

[76] Inventor: Lloyd E. Donahoo, 7386 Pomona Way, La Mesa, Calif. 92041

[21] Appl. No.: 620,958

[22] Filed: Jun. 15, 1984

[51] Int. Cl.[4] .............................................. A61F 5/40
[52] U.S. Cl. ..................................................... 128/94
[58] Field of Search .............. 128/94, DIG. 19, 91 R, 128/87 R, 83

[56] References Cited

U.S. PATENT DOCUMENTS

| 195,941 | 10/1877 | McCabe | 128/94 |
| 803,286 | 10/1905 | Hingston | 128/94 |
| 1,808,422 | 6/1931 | MacDonald | 128/94 |
| 4,023,568 | 5/1977 | Murphy | 128/83 |
| 4,198,964 | 4/1980 | Honneffer | 128/87 R |

Primary Examiner—John D. Yasko
Attorney, Agent, or Firm—Fulwider, Patton, Rieber, Lee & Utecht

[57] ABSTRACT

Arm support apparatus which includes a shoulder anchorage adapted to pass under the wearer's arm and over the shoulder. A front strap is attached to the front of the shoulder anchorage and is adapted to be attached to the wrist portion of a sling or arm cast. A rear strap is attached to the rear of the shoulder anchorage and is adapted to pass across the back of the wearer for attachment to the elbow portion of the sling or cast. The arrangement allows the weight of the supported arm to be borne by the shoulder rather then the neck.

8 Claims, 4 Drawing Figures

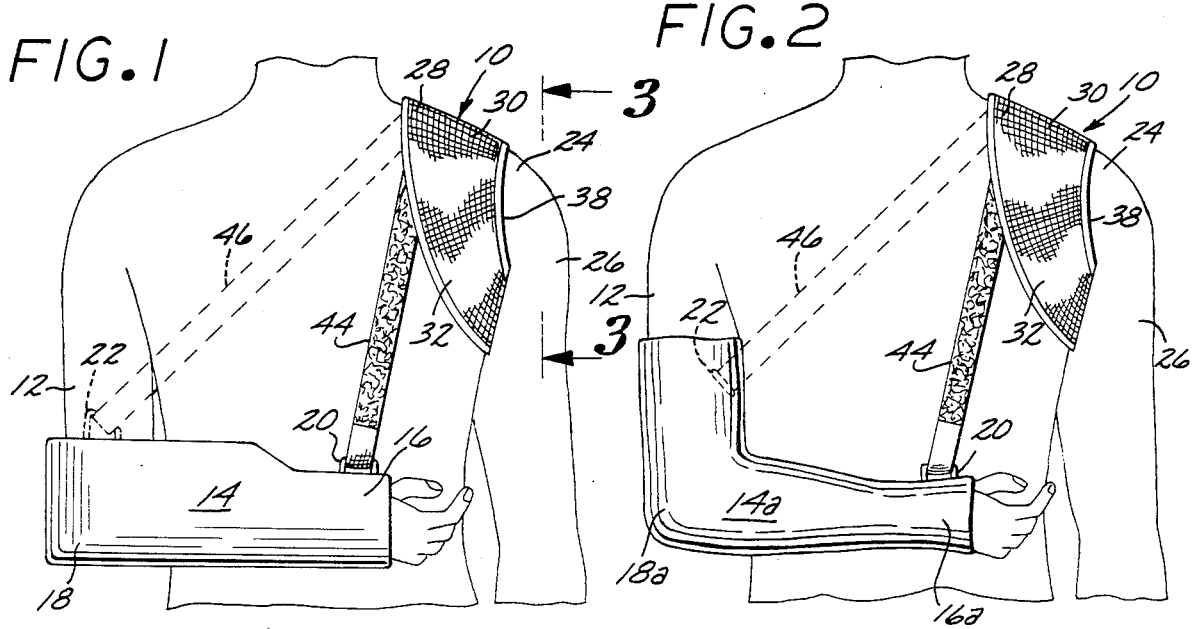
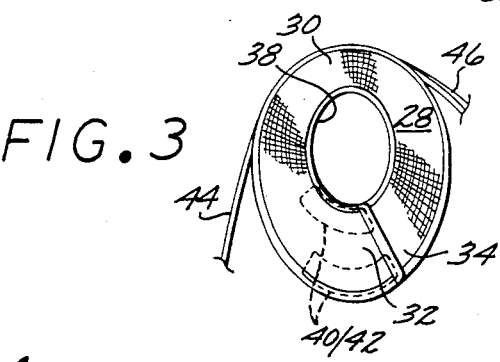
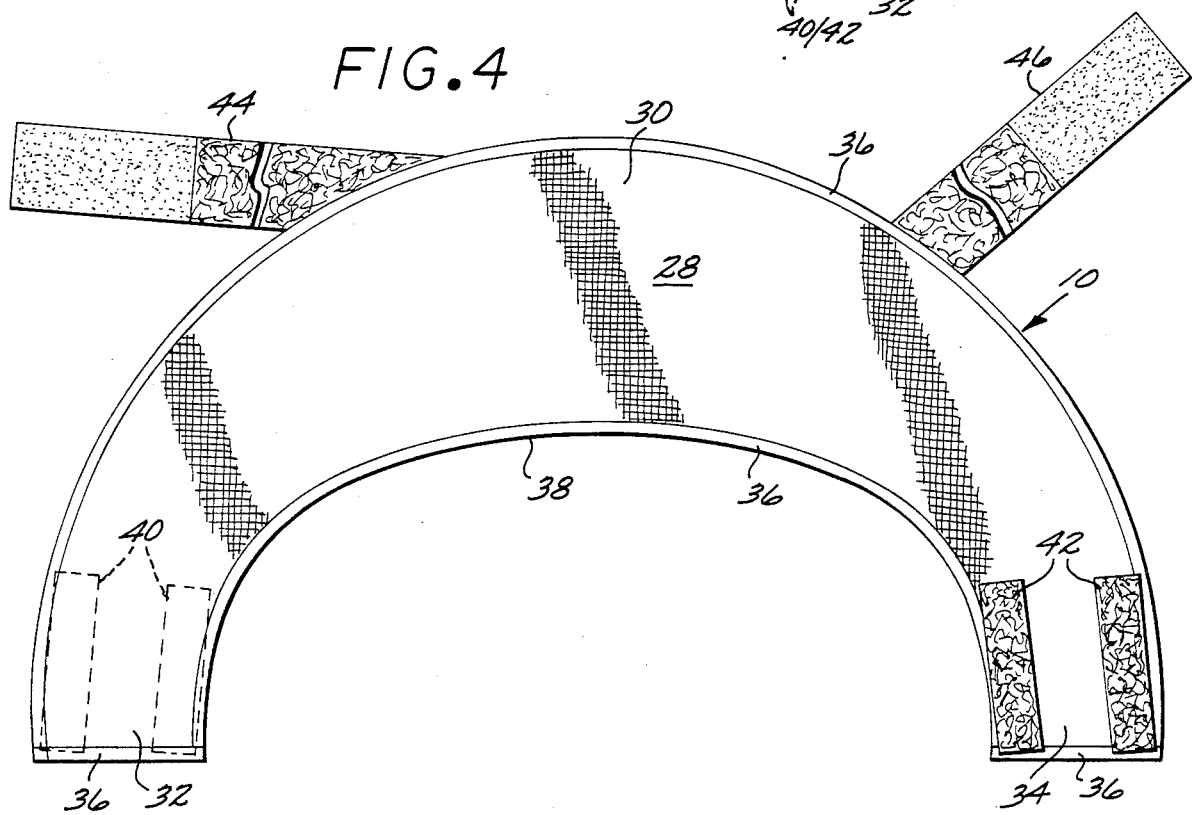

ARM SUPPORT APPARATUS

BACKGROUND OF THE INVENTION

1. Field of the Invention

The present invention relates to an arm support apparatus and more particularly an arm support apparatus for transferring the weight of the supported arm to the shoulder opposite the supported arm.

2. Description of the Prior Art

Various arm and shoulder injuries necessitate substantial immobilization of the affected arm to promote healing. The most widely used form of arm support is a sling passing around the wearer's neck and under the affected arm. A variation of this type of sling is one which is adapted for attachment to the cast which is used to immobilize the arm. In this version there are attachment or mounting rings or brackets cast in the arm cast, and supporting straps extend from the rings and about the wearer's neck. These and related arm supports place the weight of the suspended arm on the wearer's neck and often result in neck pulls, strains, and fatigue, as well as undue pressure on the carotid artery.

Other forms of prior art arm support are not supported by the neck, but typically embody a combination of an uncomfortable body harness and a complex and cumbersome arrangement of supporting straps.

SUMMARY OF THE INVENTION

According to the present invention, an arm support apparatus is provided which is relatively simply and inexpensive to fabricate, and easy to locate and position. It is adapted for use with most forms of arm slings, including arm casts having embedded mounting rings. The arm support apparatus comprises a shoulder harness or anchorage adapted to pass under the wearer's unaffected arm and over the adjacent shoulder; a front strap attached to the front of the shoulder anchorage for attachment to the wrist portion of the sling or arm cast; and a rear strap attached to the rear of the shoulder anchorage and adapted to pass across the back of the wearer for attachment to the elbow portion of the arm sling or cast whereby the weight of the affected or supported arm is borne by the shoulder opposite the supported arm, rather then by the neck.

In a preferred form of the arm support apparatus the shoulder anchorage is circumferentially discontinuous to facilitate mounting to the wearer's shoulder, the free extremities of the anchorage including self-adhering cohesive fastening means for releasably securing the extremities together.

The arrangement provides a simple and effective way of transferring the weight of the suspended arm to the shoulder opposite the arm, the front strap supporting the arm and pulling it in toward the wearer's body, while the rear strap constrains the arm against movement laterally outwardly of the wearer's body and, in association with the front strap, performs the additional important function of maintaining the shoulder anchorage in position upon the wearer's shoulder.

Other objects and features of the invention will become apparent from consideration of the following description taken in connection with the accompanying drawings.

BRIEF DESCRIPTION OF THE DRAWINGS

FIG. 1 is a front elevational view of the present arm support apparatus as it would be used in association with a typical pouch type of arm sling;

FIG. 2 is a view similar to FIG. 1, but illustrating the arm support apparatus as it would be used in association with an arm cast having integral or embedded mounting rings;

FIG. 3 is a view taken along the line 3—3 of FIG. 1; and

FIG. 4 is a top plan view of the shoulder anchorage of the arm support apparatus, as the shoulder anchorage would appear when laid flat.

DESCRIPTION OF THE PREFERRED EMBODIMENTS

Referring now to the drawings, there is illustrated an arm support apparatus 10 adapted to be worn in association with an arm sling or cast. A typical pouch type of arm sling is illustrated in FIG. 1, the wearer's affected arm 12 being disposed within the sling 14 such that the hand protrudes laterally from a wrist portion 16 of the sling, and the arm 12 extends upwardly from an elbow portion 18 of the sling.

The sling 14 includes a wrist attachment or mounting ring 20 and a similar elbow ring 22, each being attached or otherwise made integral with the material of the arm sling 14. The typical arm sling 14 is made of any suitable inelastic cloth or synthetic plastic material and consequently the rings 20 and 22 are conveniently sewn in position.

Many forms of arm sling 14 other than the pouch type are available on the market, and the present apparatus 10 is suited for use with most of these, provided only that some form of attachment or mounting means be provided for connection to the apparatus 10, as will be seen. Further, although the apparatus 10 will be described as connected to a separately obtained arm sling 14, it will be apparent that the apparatus 10 can itself include an integral arm sling similar to the arm sling 14. Further, the single rings 20 and 22 are merely exemplary of one form of attachment means. The nature of the straps or other support elements forming a part of the arm support apparatus 10 may necessitate the use of so-called "D" rings, well known in the art for adjustably holding one end of a strap or a like, or yet another form of attachment.

FIG. 2 illustrates how the single rings 20 and 22 could be embedded in a conventional fiberglass or plaster arm cast 14a rather than in the sling 14 of FIG. 1. Typically, the rings 20 and 22 would be cast in the material of the arm cast 14a when the cast is formed upon the patient's arm.

The wrist ring 20 is preferably located approximately adjacent the inner extremity of the arm sling 14, projecting upwardly from the upper side of the wrist portion 16.

The elbow ring 22 is preferably secured to the upper rearward portion of the elbow portion 18, which would be located behind the arm 12 when the arm sling 14 is in proper position. As will be seen, these points of location facilitate proper support of the arm 12, and most effectively transfer the weight of the suspended arm to the portion of the apparatus 10 located on the shoulder 24 of the unaffected or opposite arm 26.

The arm support apparatus 10 comprises, generally, a shoulder ring, harness or anchorage 28 made of any suitable substantially inelastic cloth fabric or similar material for easy laundering. The edges of the anchorage 28 include usual binding or edge reinforcement 36 to prevent unraveling of the fabric material.

The anchorage 28 is cut into an arcuate, semicircular shape or pattern, when laid flat as seen in FIG. 4. The arcuate pattern of the anchorage 28 is preferably circumferentially discontinuous to facilitate mounting to the wearer. The central portion 30 of the anchorage 28 is relatively wide, compared to the end portions 32 and 34, to pass the weight of the suspended arm 12 from the central portion 30 uniformly across the top of the shoulder.

Once the control portion 30 is located over the shoulder, the end portions 32 and 34 are overlapped beneath the arm 26 to define an armhole 38 for the unaffected arm 26. The amount and location of overlapping of the end portions 32 and 34 is such that the anchorage 28 lies snugly against the body of the wearer.

The overlapped end portions 32 and 34 are releasably secured together by the well known Velcro pile and hook components. The end portion 32 is fitted with tow strips 40 of hook material for releasable cohesive attachment to a pair of strips 42 of pile material attached to the end portion 34.

The anchorage 28 is connected to the arm sling 14, or 14a as the case may be, by elongated front and rear straps 44 and 46, each preferably made of an inextensible cloth or synthetic webbing material. The upper extremity of the front strap 44 is stitched or otherwise fixed to the front portion of the anchorage 28 adjacent the inner edge thereof, that is, the edge nearest the sling 14 and the affected arm 12. The upper end of the rear strap 46 is similarly stitched or fixed to the upper rear portion of the anchorage 28 adjacent its inner edge.

Although the stitched attachment of straps 44 and 46 to the anchorage 28 is permanent, it will be apparent that the attachment could be temporary, as by the use of D rings, single rings or Velcro attachments, as desired.

The lower extremities of the straps 44 and 46 are disposed through the rings 20 and 22, respectively, the free ends of each of the straps being doubled back upon itself for attachment to the standing portion of the strap by a Velcro fastener arrangement like that described for the anchorage end portions 32 and 34. More particularly, the standing portion of the straps 44 and 46 includes the Velcro pile material, whereas the free extremities of the straps carry the Velcro hook type material. This arrangement enables easy adjustment of the strap lengths to best suit the physical characteristics of the wearer.

The arm support apparatus 10 is extremely easy to locate in proper position, and it is very comfortable to wear. The shoulder anchorage central portion 30 is simply placed over the shoulder 24 and the end portions 32 and 34 overlapped and adhered together under the unaffected arm 26. Once the proper overlapping relationship of the end portions 32 and 34 is found for a good fit, they can be left overlapped, if desired, and the arm 26 simply withdrawn and inserted through the armhole 38. In this regard, the anchorage 28 need not be circumferentially discontinuous, but could be made in one piece, although in this form the anchorage would not then be as easily adapted to fit persons of many different sizes and statures.

Although the anchorage 28 is illustrated in position for supporting the right arm, it is easily reversible for supporting the left arm.

Once the shoulder anchorage 28 is in position, straps 44 and 46 are fitted through the rings 20 and 22, respectively, and adjusted in length to orient the arm 12 in a generally horizontal position, and with the upper portion of the arm 12 generally disposed snugly against the body.

The particular location of the attachment points for the strap 44 provides support of the arm 12 in the wrist area, accompanied by a generally downward pulling upon the anchorage 28. In contrast, the strap 46 tends to pull the arm 12 inwardly against the body, accompanied by an inward and downward pulling upon the anchorage central portion 30. These combined forces thus prevent the anchorage 28 from slipping off the wearer's shoulder, while securely supporting the arm 12 substantially immobile against the wearer's body. The tighter the strap 46 is drawn, the greater the pull of the arm 12 inwardly against the body, and the greater the inward pull upon the anchorage 28 to maintain it in position upon the shoulder 24.

From the foregoing it will be seen that by the straightforward expedient of utilizing a single shoulder ring or anchorage 28, together with straps appropriately located and fitted to connect it to an arm sling, the arm is supported, the anchorage is maintained in its fitted position, and the weight of the supported arm is entirely borne by the wearer's shoulder rather than the neck. The weight of the suspended arm is distributed uniformly across the top of that shoulder which is located opposite the affected or suspended arm.

Various modifications and changes may be made with regard to the foregoing detailed description without departing from the spirit of the invention.

I claim:

1. Arm support apparatus comprising:
   a single annular band defining a shoulder anchorage adapted to pass under the wearer's unaffected arm and over the adjacent shoulder;
   a single front strap attached to the inner margin of the front portion of said band and adapted to be attached to the wrist portion of a unitary arm support extending from the wrist to the elbow of the opposite affected arm of the wearer; and
   a single rear strap attached to the inner margin of the upper rear portion of said band and be attached to the elbow portion of the arm support for the affected arm of the wearer whereby the weight of the wearer's affected arm may be borne by the shoulder rather than the neck.

2. Arm support apparatus according to claim 1 wherein said shoulder anchorage is circumferentially discontinuous to facilitate mounting to the wearer, the free extremities of said anchorage including self-adhering cohesive fastening means for releasably securing said extremities together.

3. Arm support apparatus according to claim 1 wherein said band is made of a fabric section relatively narrow in the underarm area and relatively wide in the over-the-shoulder area for uniformly distributing over the shoulder the pressure developed by the weight of the suspended affected arm of the wearer.

4. Arm support apparatus comprising:
   a single annular band defining a shoulder anchorage adapted to pass under the wearer's unaffected arm and over the adjacent shoulder;
   a unitary arm support for supporting the full length of the opposite, affected arm of the wearer and including a wrist portion, an elbow portion, a wrist portion attachment means, and an elbow portion attachment means;

a single front strap attached at its opposite extremities to the inner margin of the front portion of said band, and to said wrist portion attachment means, respectively; and a single rear strap attached at its opposite extremities to the inner margin of the upper rear portion of said band, and to said elbow portion attachment means, respectively, for extension diagonally across the wearer's back whereby the weight of the wearer's affected arm may be borne by the shoulder rather than the neck.

5. Arm support apparatus according to claim 4 wherein said arm support is a sling, and said wrist portion attachment means and said elbow portion attachment means comprise a pair of fastening means carried by said sling.

6. Arm support apparatus according to claim 4 wherein said arm support is a cast, and said wrist portion attachment means and said elbow portion attachment means comprise a pair of fastening means integrally cast in said cast.

7. Arm support apparatus according to claim 5 wherein said front and rear straps are disposable through said pair of fastening means, respectively, and wherein the free extremities of said front and rear straps include self-adhering, cohesive portions for securing said straps upon themselves, respectively, subsequent disposition through said pair of fastening means.

8. Arm support apparatus according to claim 6 wherein said front and rear straps are disposable through said pair of fastening means, respectively, and wherein the free extremities of said front and rear straps include self-adhering, cohesive portions for securing said straps upon themselves, respectively, subsequent disposition through said pair of fastening means.

* * * * *

UNITED STATES PATENT AND TRADEMARK OFFICE
CERTIFICATE OF CORRECTION

PATENT NO. : 4,564,008

DATED : January 14, 1986

INVENTOR(S) : Lloyd E. Donahoo

It is certified that error appears in the above-identified patent and that said Letters Patent is hereby corrected as shown below:

Column 3, line 22, delete "tow" and insert "two"

Column 4, line 45, after "and" insert "adapted to"

Signed and Sealed this

First Day of April 1986

[SEAL]

Attest:

Attesting Officer

DONALD J. QUIGG

Commissioner of Patents and Trademarks